United States Patent

Walder et al.

Patent Number: 5,322,659
Date of Patent: Jun. 21, 1994

[54] METHOD FOR RENDERING A SUBSTRATE SURFACE ANTITHROMBOGENIC AND/OR ANTI-INFECTIVE

[75] Inventors: Anthony J. Walder, Franklin; Donald D. Solomon, Spring Valley; Gregory J. Mann, Dayton, all of Ohio

[73] Assignee: Becton, Dickinson and Company, Franklin Lakes, N.J.

[21] Appl. No.: 586,115

[22] Filed: Sep. 21, 1990

[51] Int. Cl.$^5$ .............................................. B29C 47/06
[52] U.S. Cl. .................................. 264/171; 264/173; 264/209.1; 264/232; 604/265
[58] Field of Search .............. 264/173, 209.1, 171, 264/177.17, 177.18, 232, 233; 424/78, 719; 604/280, 265

[56] References Cited

U.S. PATENT DOCUMENTS

| | | |
|---|---|---|
| 2,780,604 | 2/1957 | Clarke et al. |
| 3,617,344 | 11/1971 | Leininger et al. |
| 3,634,123 | 1/1972 | Eriksson et al. |
| 3,759,788 | 9/1973 | Gajewski et al. |
| 3,810,781 | 5/1974 | Eriksson et al. |
| 4,349,467 | 9/1982 | Williams et al. .................. 424/78 |
| 4,500,676 | 2/1985 | Balazs et al. ...................... 424/78 |
| 4,521,564 | 6/1985 | Solomon et al. .................. 525/54.1 |
| 4,544,547 | 10/1985 | von Bittera et al. .............. 424/78 |
| 4,581,390 | 4/1986 | Flynn ................................ 604/280 |
| 4,677,017 | 6/1987 | DeAntonis et al. ............... 428/214 |
| 4,678,660 | 7/1987 | McGary et al. ................... 425/25 |
| 4,713,402 | 12/1987 | Solomon ........................... 523/112 |
| 4,841,968 | 6/1989 | Dunn et al. ........................ 424/78 |
| 4,865,870 | 9/1989 | Hu et al. ............................ 427/2 |

OTHER PUBLICATIONS

Injection Molding Theory and Practice, Rubin, I., J. Wiley & Sons, NY, (1972) pp. 354-355.
Plastic Engineer's Data Book, Glanvill, A.B., Machinery Publishing Co., Ltd., (1971) p. 196.
Handbook of Plastics Testing Technology, Shah, V., John Wiley & Sons, NY (1984) pp. 92-93.
Modern Plastics-mid Otober Encyclopedia Issue, McGraw-Hill (1990) pp. 483, 517.
Janovic et al., Croatica Chemica Acta 51, 92 (1978).

*Primary Examiner*—Mathieu Vargot
*Attorney, Agent, or Firm*—Richard E. Brown

[57] ABSTRACT

A method to render a medical article antithrombogenic and/or anti-infective includes coextruding a base polymer with a hydrophilic laminating polymer having dispersed therein a quarternary salt complexing agent and steeping the extruded article in an aqueous solution of an antithrombogenic and/or anti-infective reagent whereby the reagent is absorbed along with water by the hydrophilic polymer and reacts with the complexing agent.

15 Claims, 2 Drawing Sheets

METHOD FOR RENDERING A SUBSTRATE SURFACE ANTITHROMBOGENIC AND/OR ANTI-INFECTIVE

BACKGROUND OF THE INVENTION

1. Field of the Invention

This invention relates to biomedical devices, and more specifically relates to a method for coating a substrate with an antithrombogenic and/or an anti-infective agent.

2. Background of the Invention

Extensive investigations have been undertaken over many years to find materials that will be biologically and chemically stable toward body fluids. This area of research has become increasingly important with the development of various objects and articles which can be in contact with blood, such as artificial organs, vascular grafts, probes, cannulas, catheters and the like.

Synthetic plastics have come to the fore as preferred materials for such articles. However, these materials have the major drawback of being thrombogenic. Thrombogenicity has conventionally been counteracted by the use of anticoagulants such as heparin. Various procedures for attachment of heparin to otherwise thrombogenic polymeric surfaces have been disclosed.

U.S. Pat. No. 4,521,564 to Solomon et al. discloses coating a polymeric article with an amine-rich surface and covalently conjugating aldehyde-actuated heparin to the amino groups thereof. Leininger et al., in U.S. Pat. No. 3,617,344 discloses a method in which a polymeric surface is chemically modified to include a chloromethyl group. Amination of the chloromethyl group provides a quarternary ammonium halide. Reaction of the halide with sodium heparin results in ionic bonding of the heparin to the surface.

A related approach has been described by Eriksson et al. in U.S. Pat. No. 3,634,123. An article having a plastic surface is heated to near or above its softening point in an aqueous solution of a cationic surface active agent, such as a long chain alkylamine or alkylenediamine hydrohalide. The solution is preacidified to a pH of 7.0 or lower. Subsequent digestion of the plastic article with an aqueous solution of heparin results in an article having about 0.1 International Unit of heparin thereon.

A further improvement is described in U.S. Pat. No. 3,810,781 to Eriksson et al., wherein heparinized plastic surfaces are stabilized with glutaraldehyde.

Williams et al., in U.S. Pat. No. 4,349,467 discloses a modification of the surface active agent-heparin method in which higher quantities of heparin are attached to a plastic surface by using more concentrated solutions of heparin. Likewise, Hu et al., in U.S. Pat. No. 4,865,870, discloses increased heparin attachment by performing the surface active agent heparin complexation at alkaline pH.

Solomon et al., in U.S. Pat. No. 4,713,402, modifies the surface active agent method by exposing the polymeric material to a solution of the surface active agent in a particular chlorofluorocarbon solvent and thereafter exposing the surface to a solution of an antithrombogenic agent, an antibiotic or a mixture thereof McGary et al. in U.S. Pat. No. 4,678,660 discloses a polyurethane article having coated thereon a layer of polyurethane alloy containing a dispersed complex of a quaternary salt and a carboxy containing antithrombogenic agent or antibiotic. The article is prepared by immersing the substrate in a solvent solution of the complex and the polyurethane alloy.

Plastic tubing rendered antithrombogenic by a phosphonium salt distributed throughout the tubing or coated thereon is disclosed by Gajewski et al. in U.S. Pat. No. 3,759,788.

While the above disclosures have resulted in significant improvements in antithrombogenicity and anti-infectiveness of polymeric surfaces, further improvements are needed. In particular, a method which avoids the use of potentially toxic solvents is needed. It is toward fulfillment of this need that this invention is directed.

SUMMARY OF THE INVENTION

A method to prepare a shaped polymeric medical article includes dispensing a blend of a hydrophilic polymer and a complexing agent for an antithrombogenic and/or anti-infective reagent and reacting the complexing agent with an antithrombogenic and/or anti-infective reagent. (In the present disclosure, the term blend is intended to include both a solution and a suspension of the complexing agent in the hydrophilic polymer and the term dispensing is intended to include molding and extruding.) In a preferred method, the blend and a polymeric base material are codispensed giving an article having the blend laminated on the base material. In the most preferred method, a tubing is prepared by extrusion or coextrusion wherein the term tubing is intended to include a solid rod and a hollow tube.

Preferred complexing agents are quaternary ammonium salts which do not undergo any substantial decomposition at the elevated temperatures required to melt the polymers for extrusion and molding. The preferred antithrombogenic reagent is heparin and the preferred anti-infective reagent is an antibiotic having a functional group suitable for complexing with the complexing agent.

In the preferred method of the invention, a substantially hydrophobic base polymer and the blend are coextruded to give a tubing having the complexing agent uniformly dispersed (hereinafter called bulk distributed) in a laminating layer of hydrophilic polymer. The tubing may then be steeped in a solvent solution, preferably a water solution, of the reagent so that the hydrophilic laminating polymer absorbs the solution and carries the reagent into the laminated layer where it reacts with the complexing agent.

The method of the invention is a significant improvement over the ionic exchange and covalent bonding methods of the prior art, most of which provide only surface coatings of heparin or antibiotic in contrast to the present invention which provides bulk distribution for greatly prolonged antithrombogenic effect. Those prior art methods which do achieve bulk distribution do so by employing an organic solvent system to dissolve a preformed complex of the heparin. These methods are uneconomical in requiring solvent and special equipment for solvent processing, and further require complete removal of the generally toxic solvent. In contrast, the method of the present invention uses simple conventional extrusion equipment and no solvent other than water. By the present method, the thickness of the laminated coating containing the heparin may easily be controlled at the extruder, a much easier method to control thickness compared to solvent based dip coating methods.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, medical articles are fabricated using particular quaternary salt agents which, when dispersed in a hydrophilic polymer, are sufficiently stable to withstand elevated fabrication temperatures without substantial decomposition. Non-limiting examples of biomedical devices contemplated to be fabricated by the method of the invention are artificial hearts, valves, membranes, grafts, syringes and preferably tubing such as catheters and obturators.

Fabrication is generally defined as the physical, mechanical or thermal manipulation of a polymer into a form such as, for example, a fiber, rod, hollow tube, sheet or film, or a device suitable for a specific application. In the present invention, molding and extruding processes are used for fabrication. In the preferred method of the invention, a base polymer and a hydrophilic laminating polymer containing the complexing agent are coextruded using a conventional apparatus 10, schematically illustrated in FIG. 1, to give a laminated rod or a multiwall hollow tubing.

Figure 1:
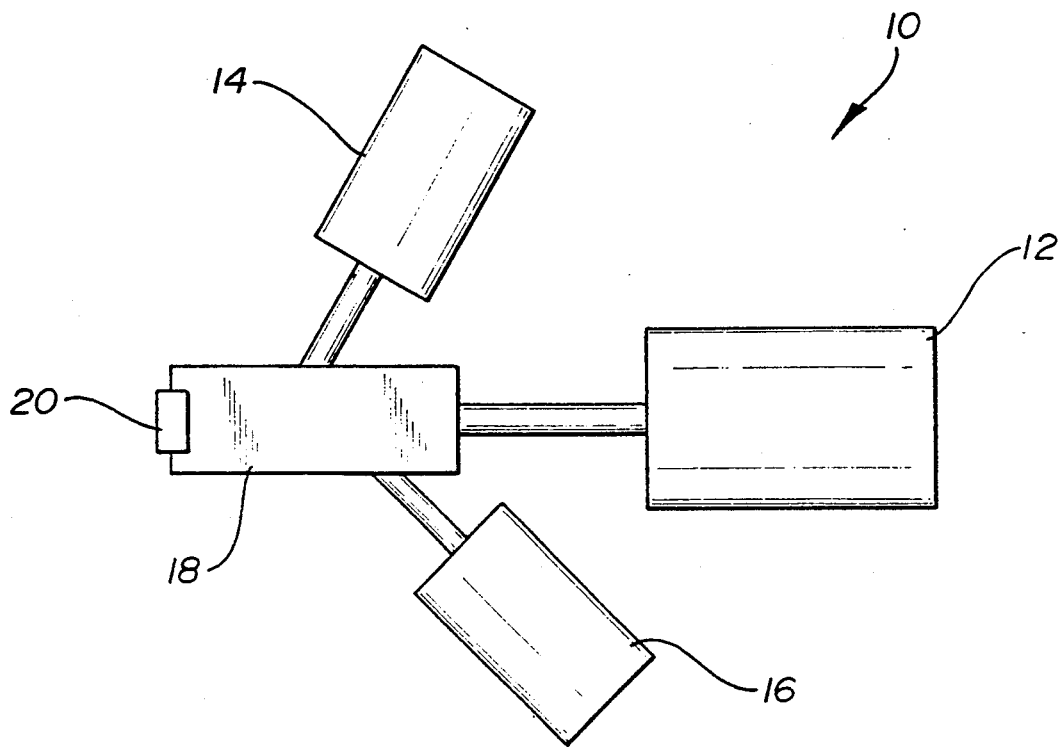
FIG. 1 is a block diagram of a coextrusion apparatus useful in the invention.

In FIG. 1, polymer melt streams from at least two of a main extruder 12 and coextruders 14 and 16 are maintained separately until combined in the forward, i.e., downstream portion of an extruder head 18, from which they subsequently pass through and emerge from a die 20. Die 20 itself, as known in the art, may be coaxial or crosshead, or, if desired for the application intended, multiple dies including both types, may be used.

When using such an apparatus, it is seen that conventional extrusion using only the main extruder 12 may give a rod or tubing having a single polymeric component, or one or more of coextruders 14 and 16 may be used to give the desired number of layers. Suitable coextrusion apparatus may be purchased for example, from Genca Cable Company, Clearwater, Fla. or from Wayne Machine and Die Company, Totowa, N.J., or if desired, custom coextrusion apparatus can be designed for fabrication of any specific article of the invention.

Figure 2:
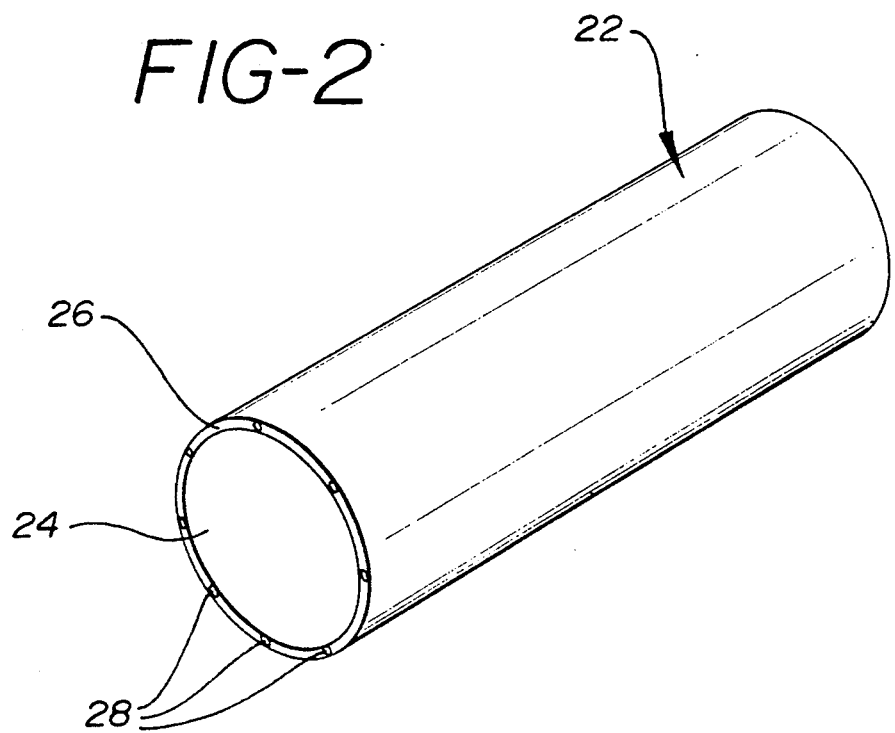
FIG. 2 is a perspective view of a solid laminated rod of the invention.

In the preferred embodiment of the invention, the base polymer and laminating polymer are coextruded from main extruder 12 and coextruder 14 or 16 to give a laminated rod. FIG. 2 shows a rod 22 of base 24 polymer having a layer of laminating polymer 26 thereon. Polymer layer 26 has dispersed therein molecules 28 of the complexing agent.

Figure 3:
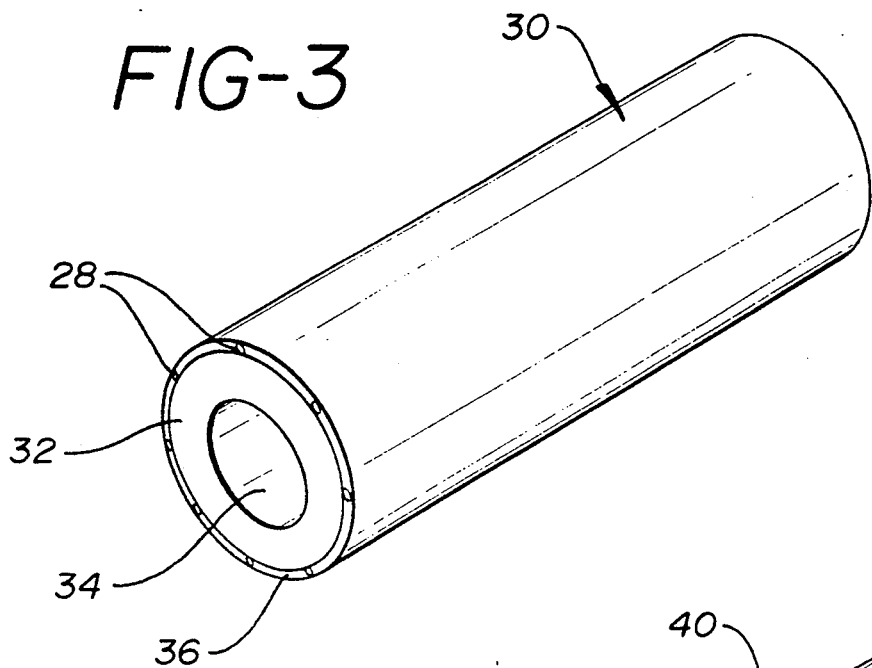
FIGS. 3-5 are perspective views of representative coextruded hollow tubes of the invention.

When the base polymer and laminating polymer are coextruded from main extruder 12 and coextruder 14 or 16 through a tubing die, a hollow tubing of the invention having a layer of laminating polymer on the base polymer may be obtained. FIG. 3 illustrates a typical two-layer hollow tubing of the invention wherein tubing 30 has base polymer layer 32 defining lumen 34 and laminating polymer 36 layered on the base polymer. If it is desired to place the laminating polymer on the lumen wall of the tubing, main extruder 12 may be used for the laminating polymer and one of the coextruders used for the base polymer.

Figure 4:
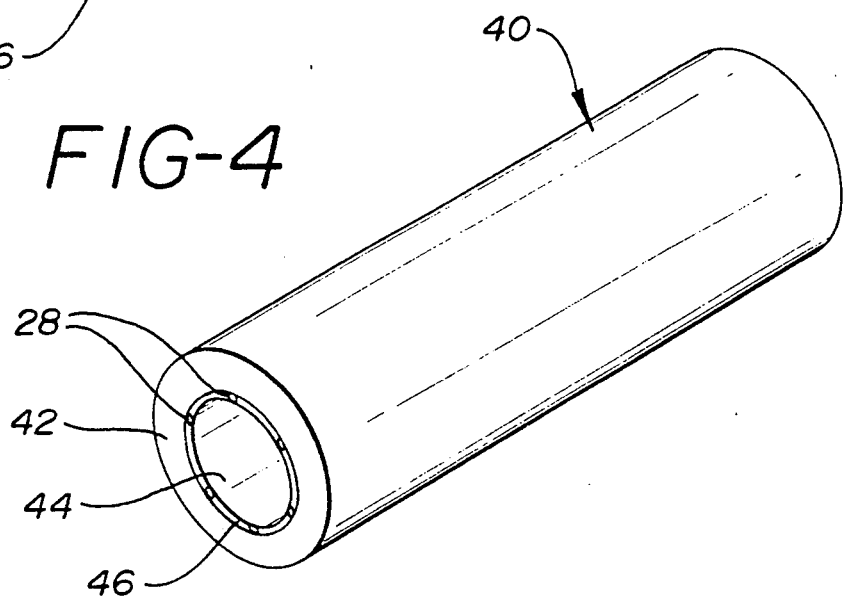
Figure 5:
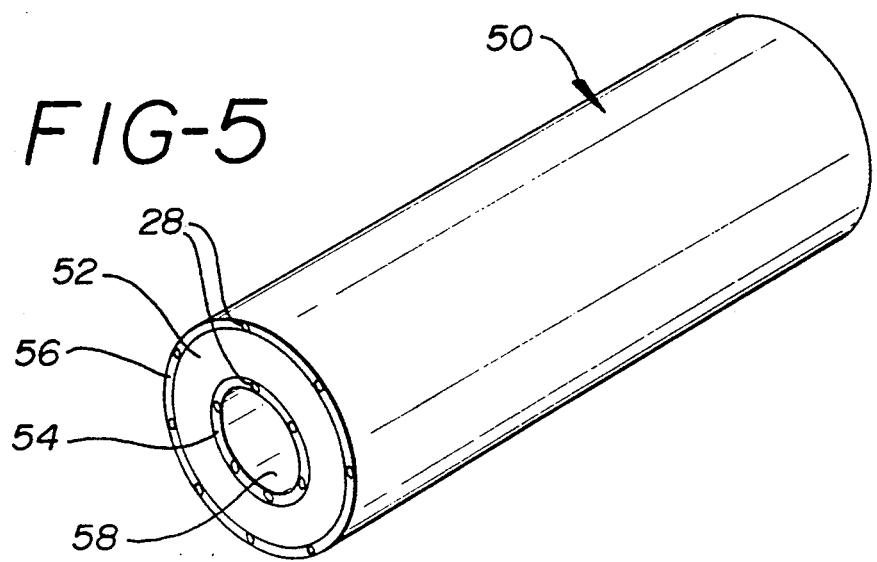

FIG. 4 illustrates a two-layer tubing 40 having polymer layer 46 defining lumen 44 laminated on base polymer layer 42. Further, a tubing having a layer of laminating polymer on both the outside surface and on the lumen wall may be obtained merely by triextrusion of the melts from the appropriate extruders. (In the present disclosure, simultaneous extrusion of three layers is termed triextrusion.) FIG. 5 shows tubing 50 having base layer 52 encapsulated by layers 54 and 56 of laminating polymer, layer 54 defining lumen 58. It is evident that the layers on the outside surface and the lumen wall may be of the same or different compositions. In each of FIGS. 3, 4 and 5, molecules 28 of the complexing agent are dispersed throughout the laminating layers.

In another embodiment of the tubing of the invention, triextrusion of the base polymer, laminating polymer and a tie-layer provides a tubing having the base and laminating layers securely bonded by an intervening tie-layer. Tie-layers are conventional in the art and are described by DeAntonis et al. in U.S. Pat. No. 4,677,017. A particularly suitable apparatus for triextrusion is the tri-layer die for medical tubing available from Genca Cable Co.

By proper selection of extruders, coextruders and dies, the number and thickness of the layers and their weight percentages may be adjusted according to the requirements of the particular article. Preferred articles of the invention have two layers and contain from 0 to 99% by weight of the base polymer and from 1 to 100% by weight of the laminating polymer. (All percentages in this disclosure are by weight unless otherwise indicated.) The most preferred article is a polyurethane tubing of 0.4 to 6.0 mm diameter with a layer of hydrophilic laminating polymer of 0.002 to 0.2, preferably about 0.02 to 0.1 mm thickness thereon.

The base polymer serves as a support material for the hydrophilic laminating polymer and provides the article with desirable mechanical properties such as tensile strength, thermoplasticity and flexibility. The invention contemplates use of any polymeric or copolymeric base material which provides these attributes, and which additionally is compatible for coextrusion with the laminating polymer. The particular choice of base polymer does not constitute a critical aspect of the invention. Suitable base polymers are polyacrylate, polystyrene, polyethylene, polypropylene, polyester, polyamide and vinyl polymers such as polyvinyl chloride and polyvinyl acetate. Preferred base polymers are thermoplastic polyurethanes, most preferably thermoplastic essentially hydrophobic polyurethanes. The most preferred base polymer is a polyurethane synthesized from a diisocyanate, a diol chain extender and a substantially hydrophobic soft segment polyol such as polytetramethylene oxide glycol.

As described above, the base polymer is coextruded with a blend of the thermoplastic hydrophilic polyurethane and the complexing agent to give an article having the desired shape. Suitable hydrophilic polymers are for example polyacrylic acids, polyhydroxyalkyl acrylates polyethyleneoxide and copolymers thereof. Preferred hydrophilic polymers are polyurethanes and polyurethane-acrylate copolymers. The most preferred hydrophilic polymers are polyurethanes having a resin hardness of about 50 A to 75D when measured under standard room conditions of 23° C. and 50% relative humidity and a water absorption capacity of 10 to 300, preferably about 60 to 150%.

As is well-known in the art, several compositional factors acting together account for water absorption in hydrophilic polyurethanes. Polyurethanes having higher soft segment contents have increased water absorption, and, within the soft segment, higher percentages of polyethylene glycol ether (relative to higher polyalkylene glycol ethers) increase water absorption. By proper selection of the hard segment-soft segment ratio and the polyglycol of the soft segment, one skilled in the art may easily prepare a polyurethane having the desired water absorption.

In accordance with the invention, a complexing agent is blended with the hydrophilic laminating polymer prior to extrusion or coextrusion with the base polymer. Any complexing agent which is stable to extrusion temperatures and shears and which forms a complex with the antithrombogenic or anti-infective agent may be used. Phosphonium salts, such as tetraphenylphosphonium chloride are suitable. Preferred complexing agents are quaternary ammonium salts of formula I.

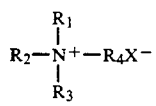

In formula I, $R_1$, $R_2$, $R_3$ and $R_4$ may independently be methyl, phenyl, benzyl or phenyl and benzyl substituted with a halogen, vinyl or alkyl group of 1-4 carbon atoms and X may be a negative ion such as phosphate, sulfate or preferably halide, most preferably chloride. Preferred quaternary ammonium salts are benzyltrimethylammonium chloride, p-chlorobenzyltrimethylammonium bromide, benzyl-vinylbenzyldimethylammonium chloride, dibenzylmethyl-vinylbenzylammonium chloride tetraphenylammonium chloride, dibenzyldimethylammonium chloride, butyl benzyltrimethylammonium chloride, tribenzylmethylammonium bromide and the like. These salts are either known or prepared by standard methods. The vinylbenzyl salts were prepared by the methods of Clarke et al., (U.S. Pat. No. 2,780,604) and Janovic et al. (Croatica Chemica Acta 51, 93 (1978).

In addition to the above salts, the invention contemplates inclusion of polymeric quaternary ammonium salt complexing agents blended with the hydrophilic laminating polymer. The polymeric complexing agent may be a homopolymer or a copolymer with another vinyl monomer such as styrene, ethylene and the like. The vinyl monomers can be selected or the copolymer can be modified to obtain the desired compatibility between the polymeric salt and the hydrophilic polymer. Preferred polymeric salts are linear, however, small amounts of crosslinked polymer do not interfere with the extrusion of the blend. Suitable polymeric salts have the structure II

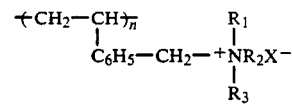

wherein $R_1$, $R_2$ and $R_3$ may independently be methyl, phenyl, benzyl or phenyl or benzyl substituted with a halogen or alkyl group of 1 to 4 carbon atoms, n may be from 2 to about 10,000, and X may be a negative ion such as phosphate, sulfate or preferably halide, most preferably chloride. These polymeric salts are either known or may be prepared by the methods of Clarke et al. and Janovic et al., supra.

The percentage of complexing agent blended into the hydrophilic laminating polymers may be about 0.001 to 3, preferably about 1 to 10, most preferably about 4 to 6%. Blending may be accomplished by dissolving the complexing agent in the laminating polymer or suspending the complexing agent in particulate form.

In accordance with the method of the invention, the base polymer and the laminating polymer having the complexing agent blended therein may be coextruded as described above at any temperature which gives melts of both polymers without causing any substantial thermal degradation of the complexing agent. Suitable temperature ranges for coextrusion are about 120 to 300° preferably about 190° to 250°, most preferably about 200° to 210° C.

After coextrusion, the complexing agent in the laminating layer may be reacted with an antithrombogenic reagent and/or an anti-infective reagent. In a preferred method, the laminated article may be steeped in a solvent solution of the reagent. Suitable solvents are alcohols such as methanol and ethanol. The preferred solvent is water. Steeping may be carried out for any suitable time and at any suitable temperature sufficient to cause the hydrophilic polymer to absorb the solvent and thereby bring the reagent into contact for reaction with the complexing agent dispersed in the laminating polymer. Preferably steeping is carried out for about 24 to 72 hours at about 25° to 70° C.

After steeping, the article may be dried by any conventional method, such as with a current of air or other gas, by heating, or merely by setting aside at ambient temperature.

The term antithrombogenic is used herein to describe any material which inhibits thrombus formation on its surface, such as by reducing platelet adhesion and/or aggregation, dissolving fibrin, enhancing passivating protein deposition, or inhibiting one or more steps within the coagulation cascade and which forms an ionic complex with particular quaternary ammonium salts. Illustrative antithrombogenic materials may be selected from the group consisting of heparin, prostaglandins, sulfated polysaccharide, and mixtures thereof. Heparin is preferred. It should be understood that these materials are used in their natural form or as salts thereof, such as the sodium or lithium salt or as a chemically modified moiety. In addition to the foregoing antithrombogenic reagents, optional supplemental amounts of antithrombogenic reagents may also be used that are not reactive with the quaternary ammonium salt but which are soluble in the water and may diffuse into the hydrophilic polymer after extrusion and thereby enhance the antithrombogenic effect. Exemplary of such materials are urokinase, streptokinase, albumin, coumadin derivatives, hirudin, dicumarol, citric acid, acetyl salicylic acid and so forth.

The term anti-infective material or reagent as used herein refers to any material which inhibits bacterial infection. Illustrative anti-infective materials may be selected from a wide range of materials that have a reactive functional group, such as a carboxyl functionality. Exemplary materials may be dibromosalicylic acid, phosphonalacetic acid, pipemidic acid, mandelic acid, nalidixic acid and antibiotics such as penicillin, oxacillin, ticarcillin, carbenicillin, cephalosporins, cefoxitin, cefazolin, dicloxacillin, cloxacillin and clavulanic acid, and mixtures thereof. Anti-infective agents which do not react with the quaternary salt but which are soluble in the solvent and thereby diffuse into the hydrophilic polymer after extrusion may be added to enhance the anti-infective effect. Exemplary of such materials are, for example, chlorhexidine, hypochlorite, chloramines, 3,4',5-tribromosalicylanilide, triphenylbismuthine, phenol and its derivatives, sodium dodecylsulfate and the like, forfomycin, bialamicol, tetracycline, polymyxins, sodium tetraborate, sulfa drugs, hydrogen peroxide and triiodide.

When the antithrombogenic and anti-infective reagents react with the complexing agent, a new complex is formed in which the anion X of formula I is replaced by the anion, preferably carboxylate, of the antithrombogenic and anti-infective reagents. This new complex, particularly a heparin complex, is larger in size and less soluble than the complexing agent. Its rate of migration to the surface of the article, while sufficient to confer antithrombogenic and anti-infective properties to the article, is decreased sufficiently by its increased size and decreased solubility to provide biological activity of long duration.

It is believed, although not yet substantiated, that the quaternary salts of the invention are stable to extrusion temperatures because they lack alkyl groups larger than methyl on the nitrogen atom. Larger alkyl groups are believed to undergo pyrolytic cleavage and decomposition at elevated temperatures with expulsion of low molecular weight fragments. These fragments escape as volatiles and cause the extruded surface to be pitted. Concurrently, the salt is degraded sufficiently to prevent or reduce subsequent complexation with the antithrombogenic and/or anti-infective agent.

The following examples are provided to further describe the invention but are not to be considered as limitative of the invention.

EXAMPLE I

A hydrophilic polyurethane, 190 g, (prepared from 4,4'-diphenylmethane diisocyanate, 1,4-butanediol and polyethyleneglycol of molecular weight 1450) was blended thoroughly with 10 g of benzyltrimethylammonium chloride. The mixture was melt processed at 205° C. and extruded into a rod of 0.076 cm diameter. The rod was smooth, and defect-free.

COMPARATIVE EXAMPLES II AND III

In the same way as described in Example I, rods were made using tridodecylmethylammonium chloride (extrusion temperature 185° C.) and benzalkonium chloride (extrusion temperature 185° C.). For both rods, the surfaces were very rough and pitted. Pitting was due to evolution of gas during extrusion due to the thermal degradation of the quaternary salts having alkyl groups larger than methyl attached to the nitrogen atom.

EXAMPLE IV

The hydrophilic polyurethane of Example I, 190 g, was blended with 10 of dibenzyldimethylammonium chloride and coextruded with a hydrophobic polyurethane (prepared using polytetramethyleneoxide glycol soft segment) at 240° to give a 0.076 cm diameter rod having a 0.057 cm diameter core of the hydrophobic polyurethane and the blend laminated thereon. The surface of the rod was smooth and defect free.

EXAMPLES V AND VI

In the same way as described in Example I rods were made using tribenzylmethylammonium chloride and tetraphenylphosphonium bromide (extrusion temperature 240° C.) to give rods which were smooth and defect free.

EXAMPLE VII

A solution of 10 g of vinylbenzylbenzyldimethylammonium chloride in 75 g of methanol was poured over 190 g of hydrophilic polyurethane pellets. After mixing, the methanol was stripped and the blend was coextruded at 185° C. with hydrophobic polyurethane to give a rod of 0.048 in. outside diameter consisting of hydrophobic polyurethane coated with 0.003 in. of the blend. The surface of the rod was smooth and defect-free.

EXAMPLE VIII

In the same way as described in Example VII, 10 g of di(vinylbenzyl)dimethyl ammonium chloride, 190 g of hydrophilic polyurethane and hydrophobic polyurethane were coextruded at 200° C. to give a tube of wall thickness 0.10 in. having an outer coating of 0.003 in. The outer surface was smooth and defect free.

EXAMPLE IX

In the same way as described in Example VII, 190 g of pellets of the hydrophilic polyurethane of Example I were mixed with a solution of 50 g polyvinylbenzylbenzyldimethyl ammonium chloride (prepared from polyvinylbenzyl chloride and dimethylbenzyl amine) in 200 g of methanol. After mixing, the methanol was stripped and the coated pellets were coextruded at 230° C. over hydrophobic polyurethane into a coated rod with an outside diameter of 0.048 in. and a coating of 0.003 in. The surface was substantially smooth and defect-free.

EXAMPLE X

In the same way as described in Example VII, 20 g of polyvinylbenzylbenzyldimethyl ammonium chloride (prepared from a polyvinylbenzyl chloride/styrene copolymer) were mixed with 190 g of hydrophilic polyurethane and the mixture pelletized at 185° C. The pellets were coextruded with a hydrophobic polyurethane at 185° C. producing a rod with a diameter of 0.025 in. and a coating thickness of 0.003 in. The surface contained granules of the polymeric quaternary salt but was free of pitting.

EXAMPLE XI

Heparinization

The rods and tubes of Examples I–X were steeped in a 10% aqueous solution of sodium heparin for 3 hours at 22° C., then dynamically leached in 1 l of 0.85% saline using an incubator shaker at 37° C. and 150 rpm for 3 days. Saline was changed daily.

EXAMPLE XII

Antithrombogenicity Study

Antithrombogenicity was determined before and after the saline rinse by measuring the activated partial thromboplastin time (APTT) according to B. A. Brown, *Hematology Principles and Procedures*, Third Edition, Lea and Febiger Co. 1984.

The following results were obtained:

| ROD OR TUBE | APTT, sec. | |
| --- | --- | --- |
|  | 0 hour | 72 hours |
| control* | >1800 | 70 |
| Example I | >1800 | >1800 |
| Example II | >1800 | 90 |
| Example III | >1800 | 85 |
| Example IV | >1800 | >1800 |
| Example V | >1800 | >1800 |
| Example VI | >1800 | 1000 |
| Example VII | >1800 | 600 |
| Example VIII | >1800 | 1000 |
| Example IX | >1800 | >1800 |
| Example X | >1800 | >1800 |

*hydrophilic polyurethane of Example I steeped in heparin but without quaternary salt.

It is seen from the data in the table that heparin was washed off the control rod and the rods made with quaternary salts having higher groups on the nitrogen, but remained firmly bound on the rods made with the salts of the invention.

EXAMPLE XIII

A control rod having a coating of the hydrophilic polyurethane of Example I on the hydrophobic polyurethane of Example IV was prepared by coextrusion. Pieces of this rod and a coated rod containing 5% of bulk distributed quaternary salt prepared as described in Example IX were immersed in a 1% aqueous solution of sodium dicloxacillin for 15 minutes. The rods were then leached by placing in normal saline for 72 hours with exchange of the saline twice daily. The rods were tested for zones of inhibition against *S. aureus* by the standard procedure as described in U.S. Pat. No. 4,678,660. The following results were obtained and are given in mm of zone of inhibition:

|  | Control Rod | Coated Rod of Example IX |
| --- | --- | --- |
| prior to immersing | 0 | 0 |
| soaked in antibiotic | 31.0 | 31.8 |
| soaked in antibiotic and leached | 0 | 14.7 |

It is seen from the above data that immersing the control rod in the antibiotic solution gives an antibiotic coating on the control, but that the coating is completely removed by the saline leach. The rod of Example IX having an extruded coating of the hydrophilic polyurethane containing quaternary salt gives a zone of inhibition prior to leaching about the same as the control rod. However, in this case, the rate of leaching of the antibiotic is such that significant killing of *S. aureus* continues after the three day leach due to the complexation of the antibiotic with the quaternary salt bulk distributed in the hydrophilic polyurethane.

Thus, the invention provides a method to render catheters, obturators and other medical articles antithrombogenic and anti-infective without resorting to methods based on toxic organic solvents which are difficult to remove.

What is claimed is:

1. A method to prepare a medical tubing which is antithrombogenic and/or anti-infective comprising coextruding a melt of substantially hydrophobic polymeric substrate with a blend of a hydrophilic polymer and a quaternary ammonium salt which is stable to the conditions of said coextruding to give a tubing of said substrate having thereon a laminated layer of said blend and contacting the tubing having the laminated layer thereon with a solution of a reagent reactive with said salt selected from the group consisting of an antithrombogenic agent, an anti-infective agent and a mixture thereof.

2. The method of claim 1 wherein said tubing is a solid rod.

3. The method of claim 1 wherein said tubing is a hollow tube.

4. The method of claim 3 wherein said hollow tube has said laminating layer on at least one of the lumen wall and the outside wall of said substrate.

5. The method of claim 1 wherein said coextruding is performed at a temperature of about 120° to 300° C.

6. The method of claim 1 wherein said polymeric substrate is selected from the group consisting of a thermoplastic polyacrylate, polystyrene, polyethylene, polypropylene, polyester, polyamide, vinyl polymer, polyurethane, polyurethaneurea and copolymers thereof.

7. The method of claim 1 wherein said hydrophilic polymer is selected from the group consisting of polyacrylic acid, poly-*p*-hydroxyethyl acrylate, polyurethane and copolymers thereof.

8. The method of claim 1 wherein said salt is selected from the group having the structure

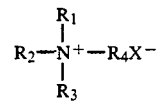

wherein $R_1$, $R_2$, $R_3$ and $R_4$ are independently selected from the group consisting of methyl, phenyl, benzyl and phenyl and benzyl substituted with a halogen, vinyl or alkyl group of 1–4 carbon atoms and X is a negative ion.

9. The method of claim 1 wherein said salt is selected from the group having the structure

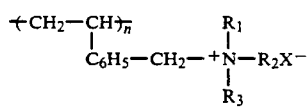

wherein $R_1$, $R_2$ and $R_3$ are independently selected from the group consisting of methyl, phenyl, benzyl and phenyl and benzyl substituted with a halogen or alkyl group of 1–4 carbon atoms, n is 2 to about 10,000 and X is a negative ion.

10. The method of claim 1 wherein said antithrombogenic agent is selected from the group consisting of heparin, prostaglandin, sulfated polysaccharide and mixtures thereof.

11. The method of claim 1 wherein said anti-infective agent is selected from the group consisting of an antibiotic, dibromosalicylic acid, phosphonalacetic acid, pipemidic acid, mandelic acid and nalidixic acid.

12. The method of claim 11 wherein said antibiotic is selected from the group consisting of penicillin, oxacillin, ticarcillin, carbenicillin, cephalosporin, cefoxitin, cefazolin, dicloxacillin, cloxacillin and clavulanic acid, and mixtures thereof.

13. A method to prepare a medical article which is antithrombogenic and/or anti-infective comprising melt dispensing a blend of thermoplastic hydrophilic polymeric melt and complexing agent which is stable to the conditions of said melt dispensing to give a shaped polymeric article and reacting the complexing agent with a reagent selected from the group consisting of an antithrombogenic agent, an anti-infective agent and a mixture thereof.

14. The method of claim 13 wherein said complexing agent is selected from the group consisting of a quaternary phosphonium salt and a quaternary ammonium salt.

15. A method to render a medical tubing antithrombogenic and/or anti-infective comprising:
a) coextruding a melt of a thermoplastic substantially hydrophobic polyurethane with a blend of a hydrophilic polyurethane and a quaternary ammonium salt which is stable to said conditions of coextruding to give a tubing having thereon a laminated layer of said blend; and
b) steeping the tubing having the laminated layer thereon in an aqueous solution of a reagent selected from the group consisting of heparin, an antibiotic and a mixture thereof whereby water and said reagent diffuse into said laminated hydrophilic polyurethane and said reagent reacts with said salt therein.

* * * * *